US006627884B2

(12) United States Patent
McCord et al.

(10) Patent No.: US 6,627,884 B2
(45) Date of Patent: Sep. 30, 2003

(54) SIMULTANEOUS FLOODING AND INSPECTION FOR CHARGE CONTROL IN AN ELECTRON BEAM INSPECTION MACHINE

(75) Inventors: Mark A. McCord, Mountain View, CA (US); David Walker, Sunol, CA (US); Jun Pei, Campbell, CA (US); Neil Richardson, Palo Alto, CA (US)

(73) Assignee: KLA-Tencor Technologies Corporation, Milpitas, CA (US)

( * ) Notice: Subject to any disclaimer, the term of this patent is extended or adjusted under 35 U.S.C. 154(b) by 49 days.

(21) Appl. No.: 09/912,732

(22) Filed: Jul. 23, 2001

(65) Prior Publication Data

US 2002/0130260 A1 Sep. 19, 2002

Related U.S. Application Data

(60) Provisional application No. 60/277,371, filed on Mar. 19, 2001.

(51) Int. Cl.[7] ................................................. G21K 7/00
(52) U.S. Cl. ....................... 250/306; 250/305; 250/302; 250/310; 250/251; 378/84; 378/85
(58) Field of Search ................................. 250/302, 305, 250/306, 310, 251; 378/84, 85

(56) References Cited

U.S. PATENT DOCUMENTS

| | | | | | |
|---|---|---|---|---|---|
| 4,453,086 | A | * | 6/1984 | Grobman | 250/307 |
| 4,645,929 | A | * | 2/1987 | Criegern et al. | 250/307 |
| 4,806,829 | A | * | 2/1989 | Nakao | 315/111.81 |
| 4,992,661 | A | * | 2/1991 | Tamura et al. | 250/307 |
| 5,023,453 | A | * | 6/1991 | Adachi et al. | 250/309 |
| 5,352,894 | A | * | 10/1994 | Yasuo | 250/305 |
| 5,444,242 | A | * | 8/1995 | Larson et al. | 250/305 |
| 6,252,412 | B1 | * | 6/2001 | Talbot et al. | 324/750 |
| 6,303,932 | B1 | * | 10/2001 | Hamamura et al. | 250/309 |

FOREIGN PATENT DOCUMENTS

| | | | | |
|---|---|---|---|---|
| FR | 2 791 776 | 1/2000 | | G01R/31/265 |
| JP | 57 147857 | 9/1982 | | H01J/37/20 |
| WO | WO 01/18843 | 3/2001 | | H01J/37/28 |

* cited by examiner

Primary Examiner—John R. Lee
Assistant Examiner—Erin-Michael Gill
(74) Attorney, Agent, or Firm—Beyer Weaver & Thomas, LLP

(57) ABSTRACT

Disclosed are methods and apparatus for simultaneously flooding a sample (e.g., a semiconductor wafer) to control charge and inspecting the sample. The apparatus includes a charged particle beam generator arranged to generate a charged particle beam substantially towards a first portion of the sample and a flood gun for generating a second beam towards a second portion of the sample. The second beam is generated substantially simultaneously with the inspection beam. The apparatus further includes a detector arranged to detect charged particles originating from the sample portion. In a further implementation, the apparatus further includes an image generator for generating an image of the first portion of the sample from the detected particles. In one embodiment, the sample is a semiconductor wafer. In a method aspect, a first area of a sample is flooded with a flood beam to control charge on a surface of the sample. A second area of the sample is inspected with an inspection beam. The second area comprises at least a portion of the first area flooded by the flood beam. The inspection beam moves in tandem with the flood beam.

In another aspect of the present invention, methods and apparatus are provided for controlling the charge buildup of an area of the sample by an electrode having a voltage applied to it and through which the flood beam and charged particles emitted from the area of the sample can pass.

30 Claims, 6 Drawing Sheets

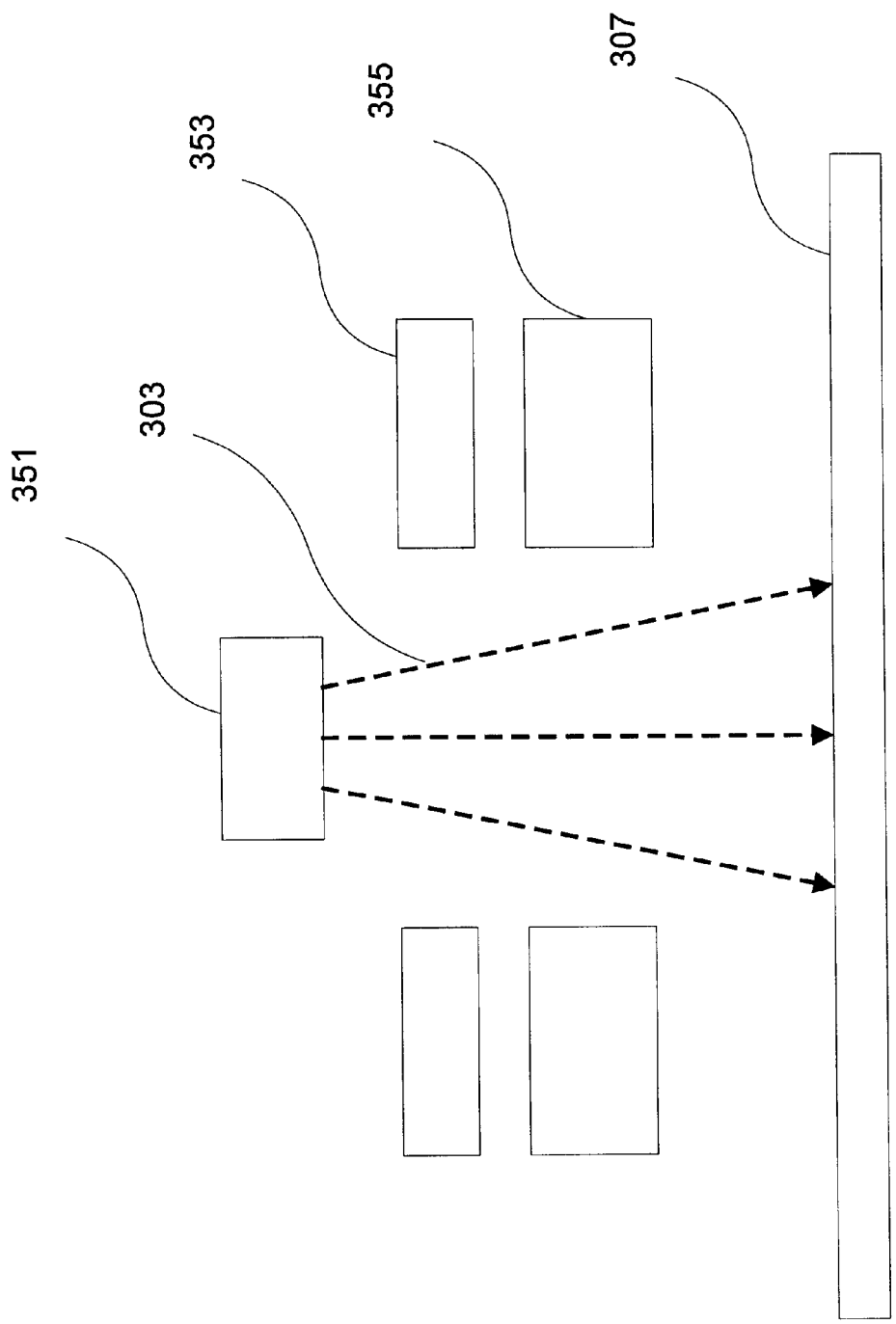

SIMULTANEOUS FLOODING AND INSPECTION FOR CHARGE CONTROL IN AN ELECTRON BEAM INSPECTION MACHINE

RELATED APPLICATION DATA

The present application claims priority from U.S. Provisional Patent Application No. 60/277,371 for SIMULTANEOUS FLOODING AND INSPECTION FOR CHARGE CONTROL IN AN ELECTRON BEAM INSPECTION MACHINE filed on Mar. 19, 2001, the entire disclosure of which is incorporated herein by reference for all purposes.

BACKGROUND OF THE INVENTION

The present invention relates generally to feature measurement in scanning electron microscopy, and more specifically to apparatus and methods for optimizing image quality by controlling the buildup of charge on a sample. The present invention may also be applied to feature measurement and image enhancement in similar instruments.

FIG. 1 is a diagrammatic representation of a conventional scanning electron microscopy configuration 100. As shown, a beam of electrons 102 is scanned over a sample 104 (e.g., a semiconductor wafer). Multiple raster scans 112 are typically performed over a small area 114 of the sample 104. The beam of electrons 102 either interact with the sample and cause an emission of secondary electrons 106 or bounce off the sample as backscattered electrons 106. The secondary electrons and/or backscattered electrons 106 are then detected by a detector 108 that is coupled with a computer system 110. The computer system 110 generates an image that is stored and/or displayed on the computer system 110.

Typically a certain amount of charge is required to provide a satisfactory image. This quantity of charge helps bring out the contrast features of the sample. Although conventional microscopy systems and techniques typically produce images having an adequate level of quality under some conditions, they produce poor quality images of the sample for some applications. For example, on a sample made of a substantially insulative material (e.g., silicon dioxide), performing one or more scans over a small area causes the sample to accumulate excess positive or negative charge in the small area relative to the rest of the sample. The excess charge generates a potential barrier for some of the secondary electrons, and this potential barrier inhibits some of the secondary electrons from reaching the detector 108. Since this excess positive charge is likely to cause a significantly smaller amount of secondary electrons to reach the detector, an image of the small area is likely to appear dark, thus obscuring image features within that small area. Alternatively, excess negative charge build up on the sample can increase the collection of secondary electrons causing the image to saturate. In some cases, a small amount of charging is desirable since it can enhance certain image features (voltage contrast) as long as it does not cause image saturation.

The excess charge remaining from a previous viewing or processing may therefore cause distortion. One solution used in SEM devices is to flood the sample with charged particles from a separate flood gun at a time separate from the inspection. This flooding equalizes the charge appearing across the sample, thus enhancing the voltage contrast images. One drawback to this flooding procedure is the need to move the stage including the entire sample to the area of the flood gun. In order to accomplish the flooding, the inspection must stop to permit movement of the sample to the area of the flood gun. This dramatically increases the overall time required for the inspection since movement and flooding of the sample may take ten minutes or more to complete. This produces an equally dramatic decrease in the throughput for the inspection process. Typically a full inspection of a sample will require hundreds of scan lines across the sample and the dissipation of charge may be required after only a few scan lines have been completed. The total time required for a sample to be inspected therefore is the sum of the separate intervals for charge dissipation (or precharging) and inspection. Consequently what is needed is a method or apparatus which will facilitate charge control on a sample without requiring the removal of the sample from the inspection beam or otherwise require the inspection beam operation to be interrupted.

As noted, voltage contrast imaging requires good control over the charge provided to the sample. The precharging step is important to provide a high quality voltage contrast image. Control over the amount of electrons emitted from the sample can affect the resolution of the image. Accordingly methods and apparatus which will provide fine control over the amount of secondary electrons reaching the detector will have a direct effect on the image quality.

SUMMARY OF THE INVENTION

Accordingly, the present invention addresses the above problems by providing apparatus and methods for controlling charge distribution on the sample (e.g., so as to improve image quality). Charge is controlled by providing an flood beam coupled to move in tandem with an inspection beam. The flood beam dissipates charge in a first area, while the inspection beam inspects a second area of the sample. In one implementation, the relative motion between the sample and the coupled inspection beam and flood beam is controlled so that the inspection beam is directed to a first area which lies entirely within a second area previously flooded with charged particles of the flood beam.

According to one aspect of the present invention, an apparatus for simultaneously flooding a sample (e.g., a semiconductor wafer) to control charge and inspecting the sample is provided. The apparatus includes a charged particle beam generator arranged to generate a charged particle inspection beam substantially towards a first portion of the sample and a flood gun for generating a second beam towards a second portion of the sample. The second beam is generated substantially simultaneously with the inspection beam. The apparatus further includes a detector arranged to detect charged particles originating from the sample portion. In a further implementation, the apparatus further includes an image generator for generating an image of the first portion of the sample from the detected particles. In one embodiment, the sample is a semiconductor wafer. In another aspect of the present invention, a wehnelt electrode is attached to the flood gun to further control charge. The wehnelt electrode is provided with an independent voltage control for fine tuning the charge control process.

In an alternative embodiment, the invention pertains to a method of inspecting a sample. A first area of a sample is flooded with a flood beam to control charge on a surface of the sample. A second area of the sample is inspected with an inspection beam. The second area comprises at least a portion of the first area flooded by the flood beam. The inspection beam moves in tandem with the flood beam.

The present invention has several associated advantages. For example, since dissipation of charge on the sample is performed in-situ and simultaneously with the inspection, throughput for the entire process is significantly increased, as compared with a process that removes the sample from inspection to flood the sample. These and other features and advantages of the present invention will be presented in more detail in the following specification of the invention and the accompanying figures which illustrate by way of example the principles of the invention.

BRIEF DESCRIPTION OF THE DRAWINGS

The present invention will be readily understood by the following detailed description in conjunction with the accompanying drawings, wherein like reference numerals designate like structural elements, and in which:

FIG. 3B is a diagrammatic representation of a flood gun portion of the scanning electron microscope system of FIG. 3A in accordance with one embodiment of the present invention.

DETAILED DESCRIPTION OF SPECIFIC EMBODIMENTS

Reference will now be made in detail to specific embodiments of the invention. Examples of these embodiments are illustrated in the accompanying drawings. While the invention will be described in conjunction with these specific embodiments, it will be understood that it is not intended to limit the invention to these embodiments. On the contrary, it is intended to cover alternatives, modifications, and equivalents as may be included within the spirit and scope of the invention as defined by the appended claims. In the following description, numerous specific details are set forth in order to provide a thorough understanding of the present invention. The present invention may be practiced without some or all of these specific details. In other instances, well known process operations have not been described in detail in order not to unnecessarily obscure the present invention.

Figure 1:
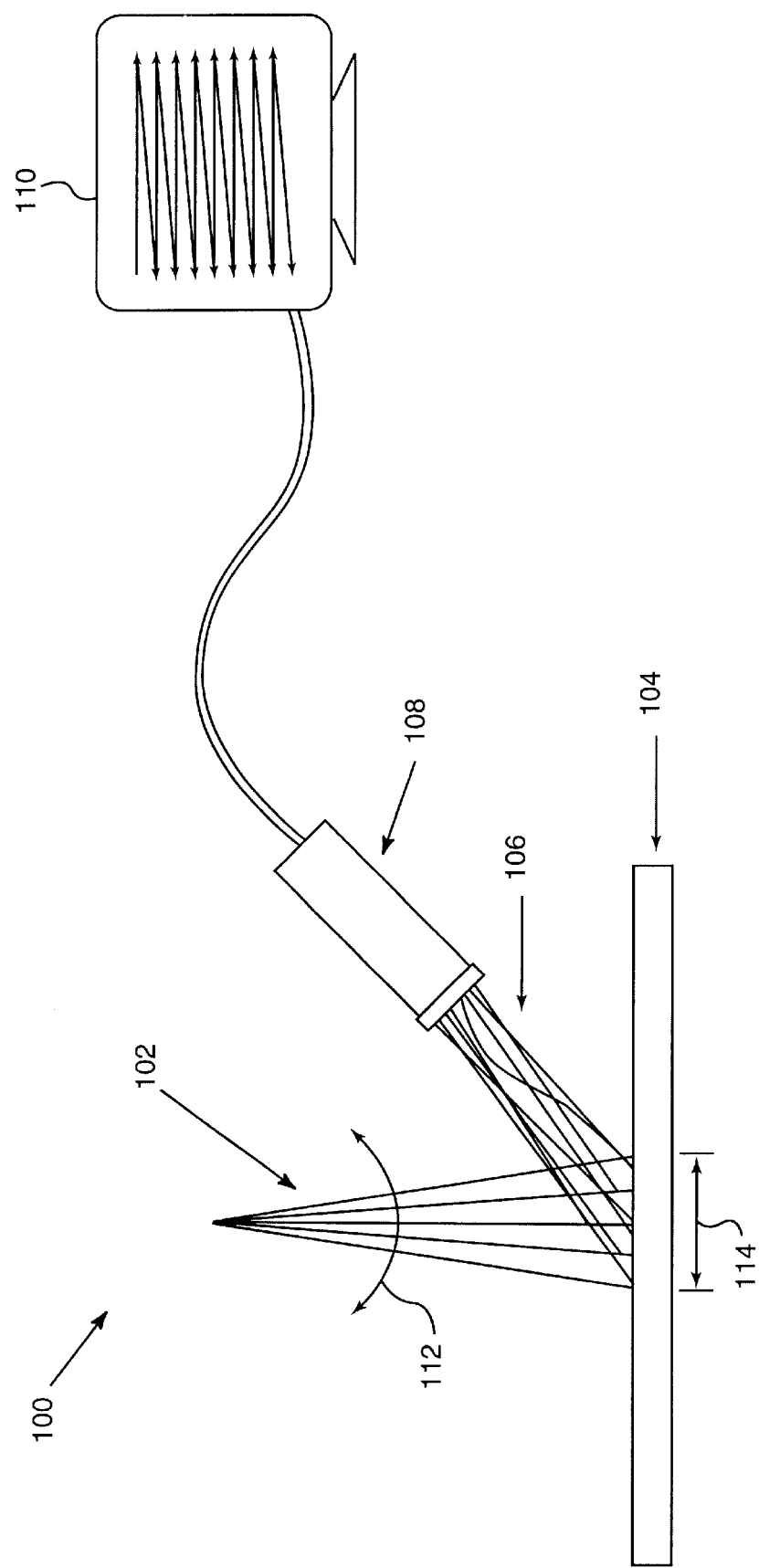
FIG. 1 is a diagrammatic representation of a conventional scanning electron microscopy configuration.
Figure 2:
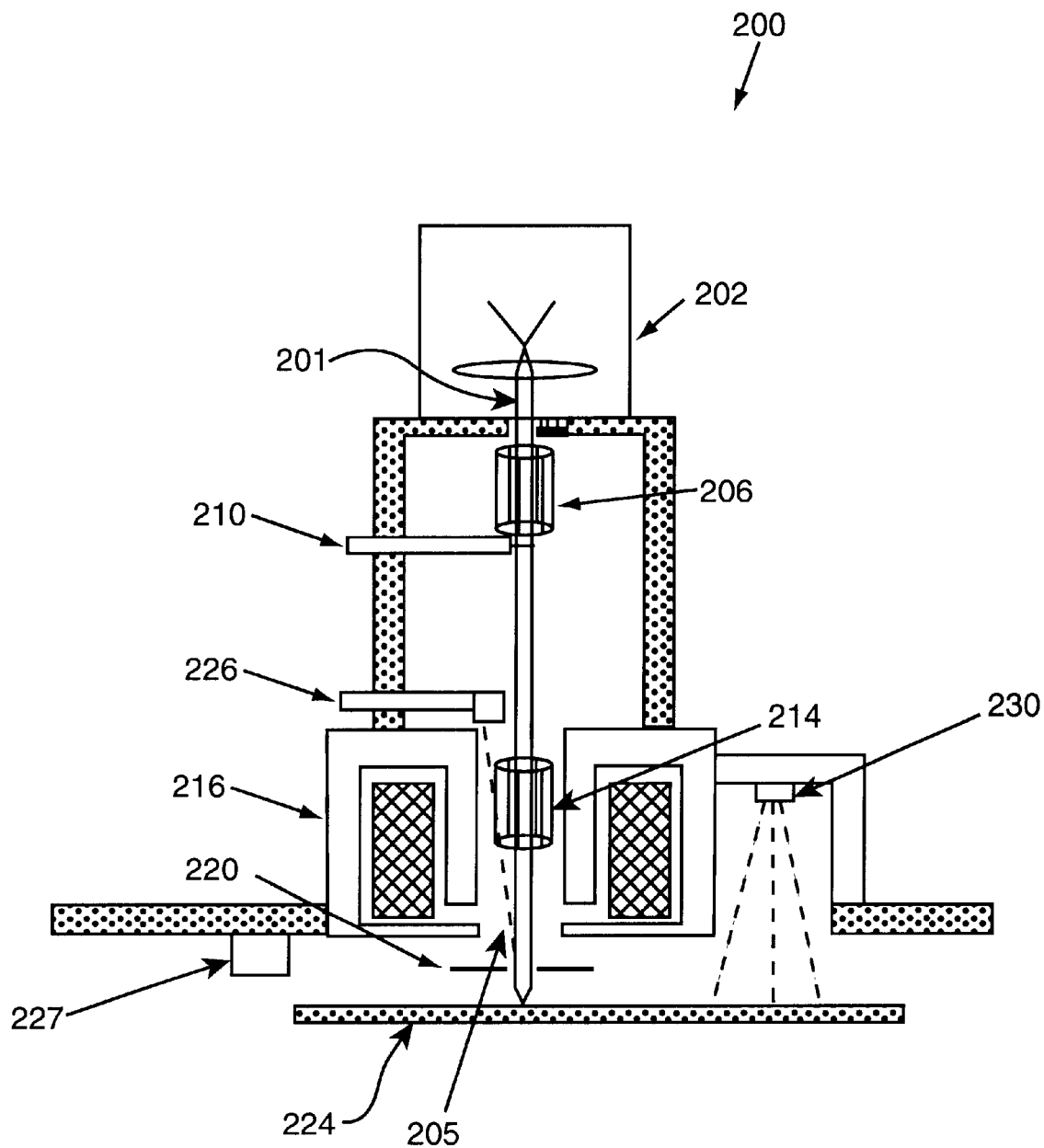
FIG. 2 is a diagrammatic representation of a scanning electron microscope (SEM) system in accordance with one embodiment of the present invention.

The present invention may be implemented within any suitable measurement device that directs charged particles towards a sample and then detects emitted particles from the sample. FIG. 2 is a diagrammatic representation of a scanning electron microscope (SEM) system 200 in accordance with one embodiment of the present invention. The SEM system 200 includes an electron beam generator (202 through 216) that generates and directs an incident electron beam 201 substantially toward an area of interest on a sample 224. The SEM system 200 also includes a detector 226 arranged to detect charged particles 205 (secondary electrons and/or backscattered electrons) emitted from the sample 224. The SEM may also include an image generator (not shown) for forming an image from the detected emitted particles. The electron beam generator and detector are further described below, along with other features of the SEM system 200.

On a specimen formed from substantially insulative material (e.g., a semiconductor or semiconductor oxide or nitride), each scan of an area of interest may result in the release of secondary electrons thereby increasing the positive charge of the area of interest with each scan. As a result of repeated scans, the area of interest (e.g., the image area) acquires a higher positive charge than the surrounding area of the specimen 224. This positive charge accumulation may form a significant potential barrier to secondary electrons and result in fewer secondary electrons reaching the detector. Thus, the area of interest may appear dark within the image. Depending on the level of positive charge on the area of interest, features within the area of interest may be difficult to discern in the image.

Additionally, when the sample is a wafer, several hundred passes are required to build an image. One unintended result of this multiple scan inspection is the scattering of charged particles beyond the area being inspected. After a small number of passes, perhaps as little as ten or even less, the stray charges build up over the entire wafer and the image of each area of the wafer degrades significantly. Accordingly, the present invention provides a mechanism for controlling this charge build up by coupling and operating a flood gun in tandem with the inspection beam. By way of a specific example, positive charge buildup resulting from an electron inspection beam may be minimized by electrons expelled or discharged from the flood gun as the inspection beam traverses across the wafer. Of course, the flood gun may also be configured to discharge positive ions for controlling negative charge build up on the sample. Alternatively, the coupled flood gun may be used to increase or decrease the charge on the surface to a predetermined value, which value depends on the particular requirements of the inspection being performed.

Any suitable arrangement may be implemented so that one or more flood guns moves in tandem with the inspection beam to thereby control charge on the sample. As depicted in FIG. 2, flood gun 230 is coupled proximate to the main inspection beam generator (e.g., components 202 through 216). This configuration permits the flood gun to discharge charged particles onto a sample portion substantially simultaneously with the inspection of another sample portion. Although the discharge occurs simultaneously with the inspection, the activities occur on two different spatial sample portions. The different sample portions may also overlap.

Figure 3A:
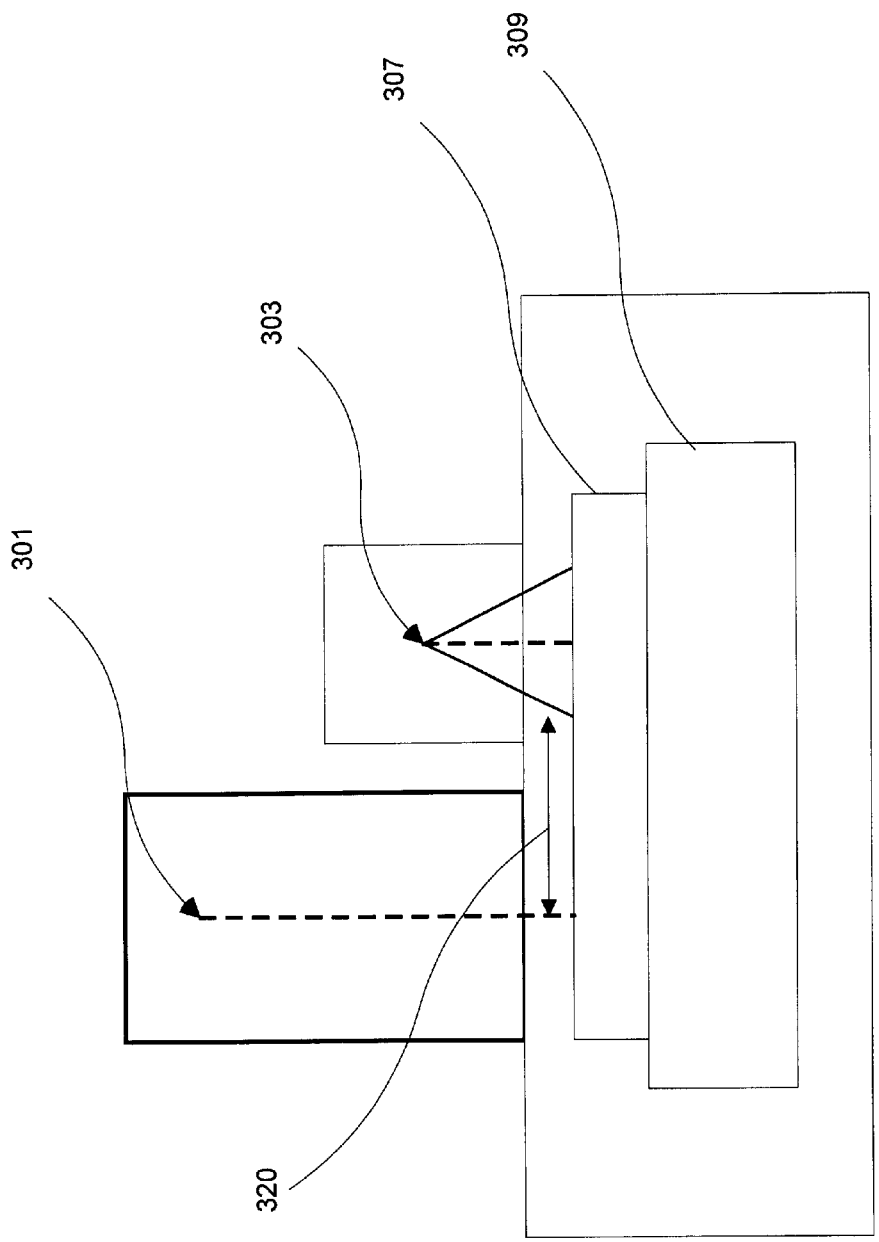
FIG. 3A is a diagrammatic representation of a portion of a scanning electron microscope (SEM) system in accordance with one embodiment of the present invention.

FIG. 3A shows a diagrammatic side view of a coupled inspection beam 301 and a flood beam 303 in accordance with one embodiment of the present invention. During operation, inspection beam 301 strikes a portion of the sample 307 and causes the emission of secondary electrons or the release of backscattered electrons from such sample portion while a second and larger sized portion (than the smaller sized portion being inspected) of the sample is subjected to a broader flood beam 303 of charged particles generated by the flood gun. The sample 307 is positioned on the stage 309 to allow both the inspection beam 301 and flood beam 303 to move over the sample 307. In other embodiments, the two beams remain stationary while the sample stage moves the sample underneath them. The position of the inspection beam 301 is coupled relative to the flood beam 303 to maintain a sufficient distance 320 between the two beams to ensure that the simultaneous operation of the flood beam 303 on a first portion of the sample does not interfere with the inspection beam 301 directed towards a second portion of the sample. For example, a distance value of between 1 mm. and 100 mm. works well.

FIG. 3B depicts an enlarged cross-sectional diagrammatic side view of the flood gun mechanism in accordance with one embodiment of the present invention. A broad flood beam of electrons 303 is shown with a blanking electrode 353 and a wehnelt 355. In a sample embodiment, the broad area beam is approximately 1 cm. in diameter, and the flood gun provides low energy electrons at 1 kev. As shown in FIG. 3A, the flood beam is not coaxial with the inspection beam, but is configured so that in one embodiment as the wafer is scanned, the flood beam 303 covers at least the same area as the inspection beam but at a slightly later time (or earlier time). In one implementation, the flood gun wehnelt 355 is provided with an independent voltage control for fine tuning the charge control process. Placing a negative voltage on the wehnelt electrode relative to the sample 307 causes charged particles to be driven down to the surface so that the surface is thereby charged more negatively. In contrast, a positive charge applied to the wehnelt electrode pulls more of the charged particles from the surface of the sample and leaves the surface more positively charged. An optimal voltage applied to the wehnelt results in about zero net charge on the surface. Thus, adjusting the voltage applied to the wehnelt 355 provides further control of the charge on the surface of the sample. This feature is especially useful when oxide is present on the sample. The voltage required on the wehnelt varies with the amount of oxide present on the surface. An optimal value for the voltage also depends on the geometry and configuration of the system. Blanking electrode 353, in one embodiment, will permit the flood gun to be disabled. For example, a voltage value of −10 volts with respect to the cathode is applied to the blanking electrode to thereby inhibit the flood beam 303 emitted from the cathode 351 from reaching the sample.

Figure 4:
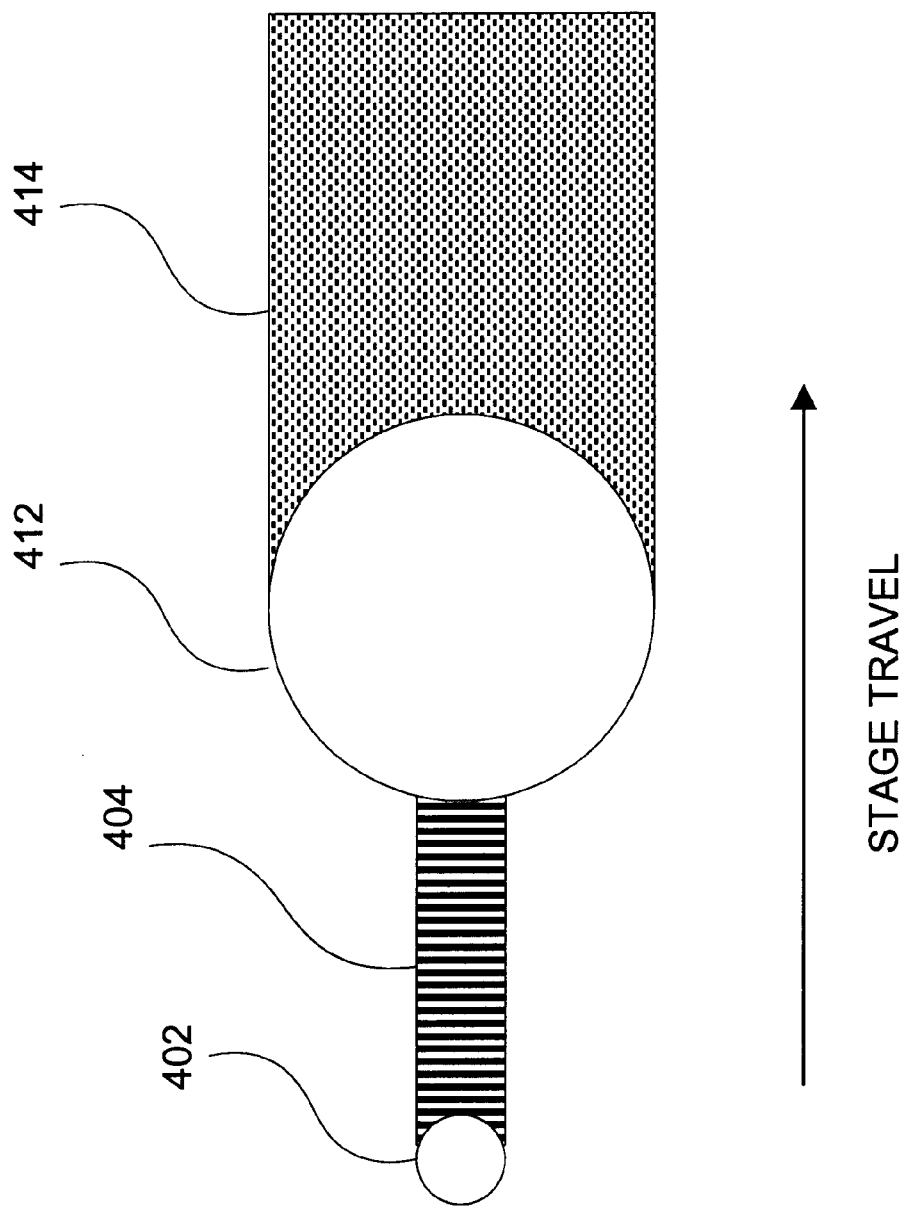
FIG. 4 is a diagrammatic representation of a first and second area of a sample in accordance with one embodiment of the present invention.

As shown in FIG. 4, the inspection beam directs charged particles to a first area 402 of the sample while simultaneously the flood gun beam directs a broader array of charged particles to a second portion 412 of the sample. Relative movement between the sample and the inspection and flood gun beams may occur in one embodiment by providing a mechanism that laterally moves the stage holding the sample as shown in FIG. 4. This movement causes the area 404 bombarded by the charged particles from the inspection beam to then be subject to a dissipating charge from the flood gun after the inspection of the sample portion occurs. In one embodiment, the larger second area 412 illuminated by the flood gun ensures that the excess charge built up in the path 404 of the inspection beam is fully dissipated. As a raster scan is performed, the dissipated surface charge area 414 provides a sample area wherein the charge is equalized. This area is now suitable for inspection by the inspection beam during the next scan line over the sample. Alternately, in another embodiment, the arrangement between the sample stage and the coupled inspection and flood beams may be configured so that a sample area is subjected to the flood beam prior to the inspection beam in order to precharge the sample area to a desired charge state.

Referring back to FIG. 2, the SEM system 200 may also be used with any number and other type of charge control mechanisms (e.g., in addition to a flood gun) such as electrodes 220 configured to control charge on the sample. Each electrode includes a hole through which the incident beam may pass. The electrode(s) are placed proximal to the sample and charged to a predetermined voltage. In general terms, the predetermined charge results in the generation of an electric field that functions to control charge on the surface of the sample. The predetermined voltage may be selected to repel some of the particles emitted from the sample back towards the sample such that charge accumulated on the surface of the sample may be controlled. For example, a portion of the secondary electrons emitted from the sample are repelled back to the sample surface to cancel positive charge build up on the sample surface. The predetermined voltage is also chosen such that some of the particles emitted from the sample pass through the hole of the electrodes to the detector. In other words, the electrode's predetermined voltage is selected to allow enough emitted particles to reach the detector and image generator such that an image may be analyzed (e.g., for defects), as well as to control charge. Several electrode configurations and electrode voltage setting techniques are described in co-pending U.S. patent application Ser. No. 09/394,133 filed Sep. 9, 1999 by McCord et al., which application is herein incorporated by reference in its entirety. As shown in FIG. 3B. a similar wehnelt electrode 355 may be placed proximal to the flood beam to finely control the surface precharge effectuated by the flood beam.

The SEM system 200 may also include a mechanism for obtaining a surface charge value of a portion of the sample after it is exposed to a charged particle beam under a set of operating conditions. The surface charge value is repeatedly obtained under different operating conditions until a predefined optimum charge value is reached or until an optimum set of operating conditions may be extrapolated. For example, it may be desirable to obtain about a zero surface charge value on the surface of the sample (e.g., positive charge build up is minimized under an optimum set of operating conditions for the electrodes 220 and flood gun 230). The metrology or inspection procedure may then proceed using the operating conditions at which the optimum charge value was reached.

Any suitable mechanism for obtaining a surface charge value of a portion of the sample may be utilized. Preferably, a non-contact measurement device is used so as to not damage the sample. In the illustrated embodiment, a measurement device 227 is positioned adjacent to the sample 224. By way of a specific example, the detector may be in one embodiment be an electrostatic voltmeter such as a non-contact Kelvin probe. One such device is the PO699 electrostatic voltmeter available from Trek Inc. of Medina, N.Y. Alternatively, the surface charge may be indirectly obtained through other measurement devices, such as an energy analyzer that measures secondary electron energy. By way of final example, an atomic force microscope (AFM) may be utilized. An AFM normally measures sample topography, but can be configured to measure surface potential.

In the illustrated embodiment, the measurement device (voltmeter) 227 is utilized to obtain a plurality of charge values under various sets of operating conditions of the SEM system 200. One or more of the operating conditions affect surface charge. That is, surface charge value changes with each set of operating conditions. Accordingly, the obtained charge values and associated operating conditions may then be utilized to determine which operating conditions will result in a desired surface charge value. Operating conditions may then be readily selected so as to obtain the desired surface charge during a metrology or inspection procedure. Any suitable type and number of operating parameters may be adjusted prior to each voltmeter reading. Several embodiments of non-contact measurement devices and several techniques for utilizing the same for controlling charge are further described in co-pending U.S. patent application Ser. No. 09/502,554 filed Feb. 10, 2000 by McCord, et al., which application is herein incorporated by reference in its entirety.

Figure 5:
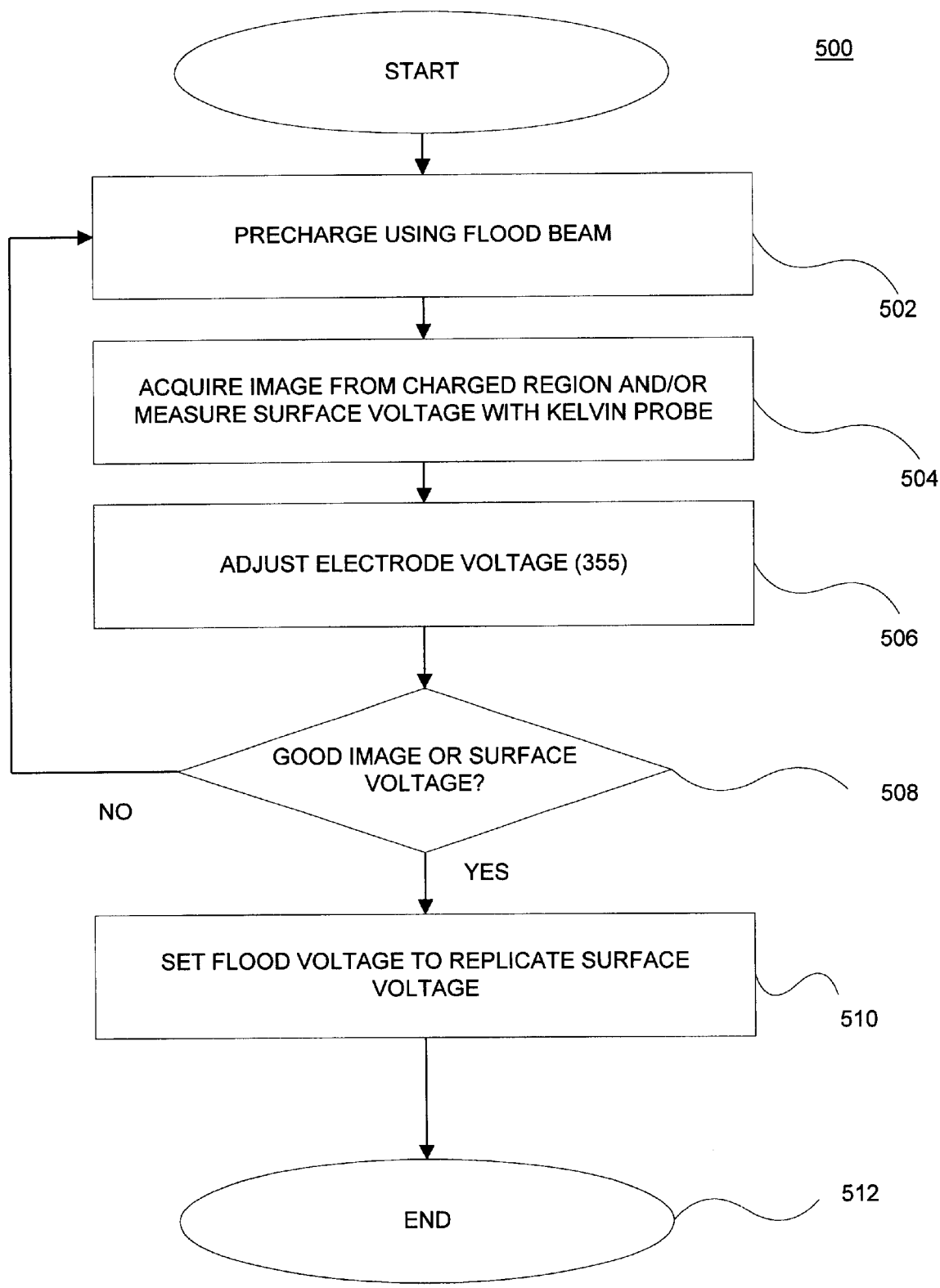
FIG. 5 is a flow chart illustrating a charge control procedure in accordance with one embodiment of the present invention.

In one implementation of the present invention, an optimal precharge is applied to the sample by independently adjusting the wehnelt voltage electrode 355 and subsequently measuring a plurality of surface voltage points. FIG. 5 is a flow chart illustrating a charge control procedure 500 in accordance with one embodiment of the present invention. This procedure 500 may be implemented by any suitable combination of hardware and/or software, such as a computer. Initially, an area of the sample is precharged by the flood beam (e.g., the flood gun moves over a particular portion of the sample ahead of the inspection beam) (502). In order to evaluate the precharge, an image is acquired form the charged region or the surface voltage is measured with a Kelvin probe (504). In one embodiment, both the image acquisition and the surface voltage measurement may simultaneously take place in order to provide a check on the alternate measurement technique. Based on these measured results, the electrode (355) voltage is adjusted to obtain a good image or a desired surface voltage (506). The amount of charge applied to the sample is evaluated in part by visually evaluating the image or by using the Kelvin probe or other technique to determine the surface voltage (508).

If the image obtained or the surface voltage measured is satisfactory, the flood voltage is then set to repeatedly obtain the same surface voltage during subsequent inspections (510). Once this voltage is determined, the fine tuning of the flood gun wehnelt voltage is completed (512), thereby permitting repeatability in the charged particle flooding of the sample surface. When the image or surface voltage measured is unsatisfactory, operations 502 through 508 are repeated with a new adjusted electrode voltage until a satisfactory image or surface voltage is obtained (508).

Any suitable mechanism for determining surface charge and determining whether such surface charge is at a desired level may be implemented. The surface charge may be determined directly by measuring the surface potential as described above with reference to FIG. 5. Alternatively, the surface charge may be obtained indirectly in numerous ways, such as measuring the energy of secondary electrons.

Referring back to FIG. 2, the electron beam generator may be arranged in any suitable configuration for generating an electron beam that will result in secondary electrons being emitted from the sample 224. As shown, the electron beam generator includes an electron source unit 202, an alignment octupole 206, a variable aperture 210, a Wien filter 214, and a magnetic objective lens 216.

The source unit 202 may be implemented in any suitable form for generating and emitting electrons. For example, the source unit 202 may be in the form of a filament that is heated such that electrons within the filament are excited and emitted from the filament. The octupole or alignment coil 206 is configured to align the beam after a particular gun lens voltage is selected. In other words, the beam may have to be moved such that it is realigned with respect to the aperture. The aperture 210 forms a hole through which the beam is directed.

The Wien filter 214 provides a B×E field (e.g., a magnetic field's direction is perpendicular and directed away from a direction of an electric field) that is normal to the electron beam's path. The Wien filter 214 applies an E force on the beam that is opposite to the B force that is applied on the beam. Thus, the Wien filter does not substantially move the beam off axis. However, the Wien filter 214 applies the E force and B force on secondary electrons emitted from the sample in a same direction that is towards the detector 226. Thus, the Wien filter 214 deflects secondary electrons towards the detector 226. The Wien filter 214 and/or octupole 206 may be configured to direct the inspection beam across an area of the sample. By setting the X and Y scan voltages, a particular beam pattern may be selected. The deflection system may include a processor that may be also configured to control voltage settings on the electrodes, as well as scan voltages, as a function of incident beam position.

The magnetic objective lens 216 provides a mechanism for focusing the beam at the sample. A plurality of electrostatic lens (not shown) may provide fast focus of the beam onto the sample surface. The SEM system 200 may include a support (not shown) or stage for supporting the sample 224.

The SEM system 200 includes an electron detector 226 which, as previously described, may be configured to determine the voltage of the secondary electrons. The SEM system 200 also includes an image generator (not shown) arranged to receive the detected signal and generate and/or store an image. The detected signal is then used to generate the image. Thus, the SEM system 200 may also include an analog to digital converter for converting the detected signal into a digital signal. The SEM system 200 may also include a computer system for processing the image frame data to generate an image of the sample. For example, successive image frame data may be averaged together to create the image. The computer may also be configured to set various operating conditions, analyze surface voltage values under various operating conditions, and determine optimum operating conditions based on such analysis.

In addition, embodiments of the present invention further relate to computer storage products with a computer-readable medium that have computer code thereon for performing various computer-implemented operations. The media and computer code may be those specially designed and constructed for the purposes of the present invention, or they may be of the kind well known and available to those having skill in the computer software arts. Examples of computer-readable media include, but are not limited to: magnetic media such as hard disks, floppy disks, and magnetic tape; optical media such as CD-ROMs and holographic devices; magneto-optical media such as floptical disks; and hardware devices that are specially configured to store and execute program code, such as application-specific integrated circuits (ASICs), programmable logic devices (PLDs) and ROM and RAM devices. Examples of computer code include machine code, such as produced by a compiler, and files containing higher level code that are executed by a computer using an interpreter.

Although the foregoing invention has been described in some detail for purposes of clarity of understanding, it will be apparent that certain changes and modifications may be practiced within the scope of the appended claims. It should be noted that there are many alternative ways of implementing both the process and apparatus of the present invention. For example, the sample may be any substance or object that is suitable for charged particle inspection, such as a semiconductor wafer, a reticle, or a biological sample. Additionally, the present invention may be especially useful in inspecting thin film heads within hard disks, which are being designed with smaller and smaller dimensions.

Accordingly, the present embodiments are to be considered as illustrative and not restrictive, and the invention is not to be limited to the details given herein, but may be modified within the scope and equivalents of the appended claims.

What is claimed is:

1. An apparatus for controlling charge on a sample, the apparatus comprising:

an electron beam generator configured to generate an inspection beam of electrons towards a first portion of a sample;

a flood gun configured to generate a flood beam of charged particles towards a second portion of the sample to control charge on the surface of the second portion of the sample, the flood beam being generated substantially simultaneously with the inspection beam, wherein the flood beam is coupled to move with the inspection beam; and a detector arranged to detect charged particles originating from the first portion of the sample.

2. The apparatus as recited in claim 1 further comprising an image generator for generating an image of the first portion of the sample from the detected particles.

3. The apparatus as recited in claim 1, wherein the charged particles are electrons.

4. The apparatus as recited in claim 1, wherein the sample is a semiconductor wafer.

5. The apparatus as recited in claim 1, wherein the first portion is larger than the second portion.

6. The apparatus as recited in claim 1, further comprising an electrode having a hole through which the flood beam of charged particles and electrons emitted from the second portion of the sample can pass, said electrode further having an independent voltage control for controlling the charge buildup on the second portion of the sample.

7. The apparatus as recited in claim 6 further comprising a sample positioning mechanism configured to provide relative movement between the sample and the coupled inspection beam and flood beam.

8. The apparatus as recited in claim 7 wherein the flood gun, inspection beam generator, and sample positioning mechanism are further configured so that the flooding of the first portion occurs prior to the inspecting of the second portion.

9. The apparatus as recited in claim 7 wherein the flood gun, electron beam generator, and wafer positioning mechanism are further configured so that the flooding of the first portion occurs after the inspecting of the second portion.

10. The apparatus as recited in claim 7 wherein the flood gun, inspection beam generator, and sample positioning mechanism are further configured to allow the electron beam to move across the wafer in a scan line.

11. The apparatus as recited in claim 10 wherein the scan line forms a raster pattern.

12. The apparatus as recited in claim 1 wherein the flood beam is coupled to move in tandem with the electron beam generator.

13. A method of inspecting a sample comprising:

flooding a first area of the sample with a flood beam of charged particles to control charge on a surface of the sample; and inspecting simultaneously with the flooding a second area with an inspection beam of electrons, the second area comprising at least a portion of the sample previously flooded by the flood beam, said inspection beam moving in tandem with the flood beam.

14. The method of inspecting a sample as recited in claim 13, wherein the flooding of the first area is to precharge the surface of the sample.

15. The method of inspecting a sample as recited in claim 13, wherein the flooding of the first area is to neutralize charge on the surface of the sample.

16. The method of inspecting a sample as recited in claim 13, wherein the flooding of the first area is to neutralize charge build up on the surface of the sample caused by inspecting the sample.

17. The method of inspecting a sample as recited in claim 13, the method further comprising:

providing relative motion between the sample and the tandem inspection beam and flood beam so that the inspection beam moves in scan lines to inspect the entire sample.

18. The method of inspecting a sample as recited in claim 17, wherein the scan lines form a raster pattern.

19. The method of inspecting a sample as recited in claim 13, wherein the flooding of the first area occurs prior to the inspecting of the second area.

20. The method of inspecting in a sample as recited in claim 13, wherein the flooding of the first area occurs after the inspecting of the second area.

21. The method of inspecting in a sample as recited in claim 13, further comprising applying a voltage to an electrode positioned to control charged particles emitted from a first portion of the sample.

22. The method as recited in claim 13 further comprising subsequently inspecting the first area simultaneously with the flooding of a third area of the sample by the flood beam.

23. An apparatus for controlling charge on a sample, the apparatus comprising:

an electron beam generator configured to generate an inspection beam of electrons towards a sample to cause emission of electrons from the sample;

a flood gun configured to generate a flood beam of charged particles towards a first portion of the sample to control charge on the surface of the first portion of the sample, and an electrode having a hole through which the flood beam of charged particles and electrons emitted from the sample can pass, said electrode further having an independent voltage control for controlling the charge buildup on the first portion of the sample.

24. The apparatus as recited in claim 23, further comprising a detector arranged to detect charged particles originating from the second portion of the sample.

25. The apparatus as recited in claim 23, further comprising an image generator for generating an image of the second portion of the sample from the detected particles.

26. The apparatus as recited in claim 23 wherein the charged particles are electrons.

27. The apparatus as recited in claim 23 wherein the sample is a semiconductor wafer.

28. The apparatus as recited in claim 23 further comprising a sample positioning mechanism configured to provide relative movement between the sample and the flood gun.

29. The apparatus as recited in claim 23 wherein the flood gun and sample positioning mechanism are configured so that the flood gun remains stationary while the sample positioning mechanism moves the sample underneath the first beam from the flood gun.

30. An apparatus for controlling charge on a sample, the apparatus comprising:

an electron beam generator configured to generate an inspection beam of electrons for impinging on a first portion of a sample;

a flood gun configured to generate a flood beam of charged particles impinging on a second portion of the sample to control charge on the surface of the second portion of the sample, wherein the flood beam and the inspection beam are coupled to move in tandem relative to the sample; and a detector arranged to detect charged particles originating from the first portion of the sample as a result of the impingement of the inspection beam and wherein the detection occurs substantially simultaneously with the generation of the flood beam of charged particles impinging on the second portion of the sample.

* * * * *